US005487607A

United States Patent [19]
Makita et al.

[11] Patent Number: 5,487,607
[45] Date of Patent: Jan. 30, 1996

[54] RADIATION CLINICAL THERMOMETER

[75] Inventors: Shigeru Makita; Yoshihiko Sano, both of Kyoto, Japan; Yasushi Nakamura, Irvine, Calif.; Hiroyuki Ota, Shiga, Japan

[73] Assignee: Omron Corporation, Kyoto, Japan

[21] Appl. No.: 176,459

[22] Filed: Dec. 29, 1993

Related U.S. Application Data

[63] Continuation-in-part of Ser. No. 45,054, Apr. 7, 1993, abandoned.

[30] Foreign Application Priority Data

Apr. 8, 1992 [JP] Japan ..................... 4-86738

[51] Int. Cl.$^6$ ................ G01K 1/08; G01J 5/02
[52] U.S. Cl. ............ 374/158; 128/736; 128/664; 374/209; 374/121
[58] Field of Search ................ 374/121, 158, 374/208, 209; 128/664, 736

[56] References Cited

U.S. PATENT DOCUMENTS

| | | | |
|---|---|---|---|
| 4,634,294 | 1/1987 | Christol et al. | 374/170 |
| 4,743,122 | 5/1988 | Yamano et al. | 374/208 |
| 4,784,149 | 11/1988 | Berman et al. | 374/158 |
| 4,895,164 | 1/1990 | Wood | 128/736 |
| 4,911,559 | 3/1990 | Meyst et al. | 374/158 |
| 4,993,424 | 2/1991 | Suszynski et al. | 128/736 |
| 5,046,482 | 9/1991 | Everest | 374/158 |
| 5,340,215 | 8/1994 | Makita et al. | 374/208 |

FOREIGN PATENT DOCUMENTS

| | | |
|---|---|---|
| 0445784A2 | 9/1991 | European Pat. Off. . |
| WO92/11800 | 7/1992 | WIPO . |

OTHER PUBLICATIONS

European Search Report (2 pp.).

*Primary Examiner*—Diego F. F. Gutierrez
*Attorney, Agent, or Firm*—Foley & Lardner

[57] ABSTRACT

A radiation clinical thermometer includes a moveable probe which actuates a start switch when inserted into a patients ear. The radiation clinical thermometer also includes a probe cover device for dismounting a probe cover from the probe. The probe cover device is operatively connected in circuit with the start switch to only allow operation of the thermometer when the probe cover device is in a position indicating that a probe cover is mounted on the probe. The thermometer also includes time delay devices which preclude operating the thermometer unless the start switch or the probe cover detection device is in a predetermined position for a predetermined amount of time.

13 Claims, 7 Drawing Sheets

RADIATION CLINICAL THERMOMETER

CROSS-REFERENCE TO RELATED APPLICATIONS

This application is a Continuation-In-Part of U.S. patent application Ser. No. 08/045,054 filed Apr. 7, 1993, now abandoned.

BACKGROUND OF THE INVENTION

1. Field of the Invention

This invention relates to a radiation clinical thermometer, and more particularly to an improved radiation clinical thermometer for measuring human body temperature by sensing infrared radiation.

2. Discussion of the Related Art

A conventional radiation clinical thermometer includes a body housing enclosing circuitry and a power source, a probe externally projecting from the housing and internally enclosing an infrared radiation sensor (temperature sensor), and a probe switch. The sensor is designed to collect infrared radiation through the probe. An example of such a conventional radiation clinical thermometer is disclosed in U.S. Pat. No. 4,895,164. For the measurement of a body temperature, the conventional radiation clinical thermometer is used by inserting its probe into an ear opening. When the thermometer is not in use, a cap is mounted on the probe. For the prevention of stains and for sanitation purposes, the probe is mounted by a probe cover for use in measuring.

Conventional clinical thermometers have the disadvantage that unnecessary measurement is initiated upon the depression of a start switch even if a probe cover is not mounted on the probe. If a probe cover is mounted on the probe in the power-on state of a conventional radiation clinical thermometer which is designed to actuate the temperature measuring start switch in response to the movement of the probe, the probe moves backwardly as the probe is pushed into the ear opening. The backward movement of the probe turns on the probe start switch for immediate measurement of body temperature. If, however, during the power on state of the thermometer, the probe is unintentionally pushed when the cover is not mounted thereon, or is pushed backwardly in the process of the probe cover being mounted thereon, temperature measurement is initiated so as to execute an unnecessary measurement of body temperature in spite of the unmounted state of the cover. Such initiation of measurement by unintentionally depressing the probe is prevented if the cover is carefully and precisely mounted. However, it is often the case that mounting is carelessly executed and unnecessary temperature measurement occurs. Since the temperature measurement circuitry is designed to operate to take into account the attenuation of the infrared radiation by the cover, if no cover is used, the thermometer will display a temperature measurement result that is higher than the actual temperature so that a precise body temperature measurement is not obtained.

SUMMARY OF THE INVENTION

It is an object of this invention to provide an improved radiation clinical thermometer inhibiting measurement when the probe cover is not mounted thereon to avoid unnecessary and inaccurate temperature measurement.

According to this invention, there is provided a radiation clinical thermometer, in which a probe cover removable means for unmounting a probe cover mounted on a probe is engaged with the probe cover during a forward-and-backward movement relative to the probe. Further, a probe cover mount detection switch is disposed to be actuated in response to the movement of the probe cover removable means, whereby temperature measurement is not initiated, even if a body temperature measurement start signal is produced by a probe start switch, when a signal representing an unmounted probe cover is generated by the probe cover mount detection switch.

According to this radiation clinical thermometer, when the probe cover is not mounted on the probe, the probe cover mount detection switch (called "cover switch" hereinafter) generates a cover unmount signal in response to a position of the probe cover removable means so that temperature measurement is not initiated in the presence of the cover unmount signal even if the start switch is depressed (turned on). If the cover is mounted, the cover switch generates a cover mount signal in response to the position of the probe cover removable means so as to be ready for measurement so that upon turning on the start switch, the body temperature measurement is initiated based on infrared radiation collected from the ear opening through the probe.

One example of a thermometer which accomplishes the above object includes: a body housing; a temperature measuring circuit disposed in the body housing; a probe secured to the body housing; a temperature sensor disposed in the probe; a power supply connected in circuit with the temperature measuring circuit and the temperature sensor; a probe cover removable means for dismounting a probe cover from the probe, the probe cover removable means including a member moveable from a first position in which the probe cover is not mounted on the probe to a second position in which the probe cover is mounted on the probe; and a probe cover mount detection switch connected in circuit with the temperature measuring circuit and engageable the probe cover removable means when the probe cover removable means is moved into the second position thereby actuating the probe cover mount detection switch, the probe cover mount detection switch enabling operation of the thermometer only when the probe cover removable means is in the second position, whereby operation of the thermometer takes place only when the probe cover is mounted on the probe.

In accordance with another aspect of the invention, a radiation clinical thermometer further includes a counting means for delaying the initiation of temperature measurement unless a predetermined time has elapsed after the cover unmount signal is no longer generated, i.e., after a cover mount signal is generated. In this embodiment, temperature measurement is not possible until a predetermined time has elapsed after mounting of the probe cover, thereby preventing unnecessary measurement due to the inadvertent instantaneous and intermittent closing and opening of the cover switch which may occur during the mounting of the probe cover on the probe. Moreover, the thermometer construction may be such that the probe is adapted to be moved in a forward-and-backward direction and the probe start switch is designed to be actuated in response to the backward movement of the probe. In this manner, when the probe moves backward by inserting the probe into an ear, the probe start switch is turned on for initiating body temperature measurement, but only after the cover mount signal has been generated for the predetermined time.

The above delay feature is accomplished by providing a radiation clinical thermometer which includes: means for determining if the probe cover mount detection switch has been actuated for a predetermined period of time and for enabling operation of the thermometer only when the probe cover mount detection switch has been actuated for the predetermined period of time and the probe cover is in mounted on the probe.

Yet another object of the invention is to provide a radiation clinical thermometer which prevents temperature measurement unless a probe detection start switch was in an open position for a predetermined period of time prior to its being closed. This object is met by providing a radiation clinical thermometer including a body housing; a temperature measuring circuit disposed in the body housing; a temperature sensor; a start switch connecting in circuit with a power source, the temperature sensor and the temperature measuring circuit; a probe surrounding the temperature sensor and being movably secured in the body housing, the probe biased for movement outwardly of the body housing in a projected state prior to temperature measurement in which the start switch is not actuated and moveable to a retracted state by insertion of the probe into an ear opening of a patient, the retracted state actuating the start switch to enable operation of the thermometer; means for preventing enablement of operation of the thermometer upon actuation of the start switch unless prior to actuation of the start switch, the start switch was not actuated for a predetermined period of time.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out in the appended claims.

BRIEF DESCRIPTION OF THE DRAWINGS

The accompanying drawings, which are incorporated in and constitute a part of the specification, illustrate a presently preferred embodiment of the invention, and, together with the general description given above and the detailed description of the preferred embodiment given below, serve to explain the principles of the invention.

DETAILED DESCRIPTION OF THE PREFERRED EMBODIMENTS

Figure 1:
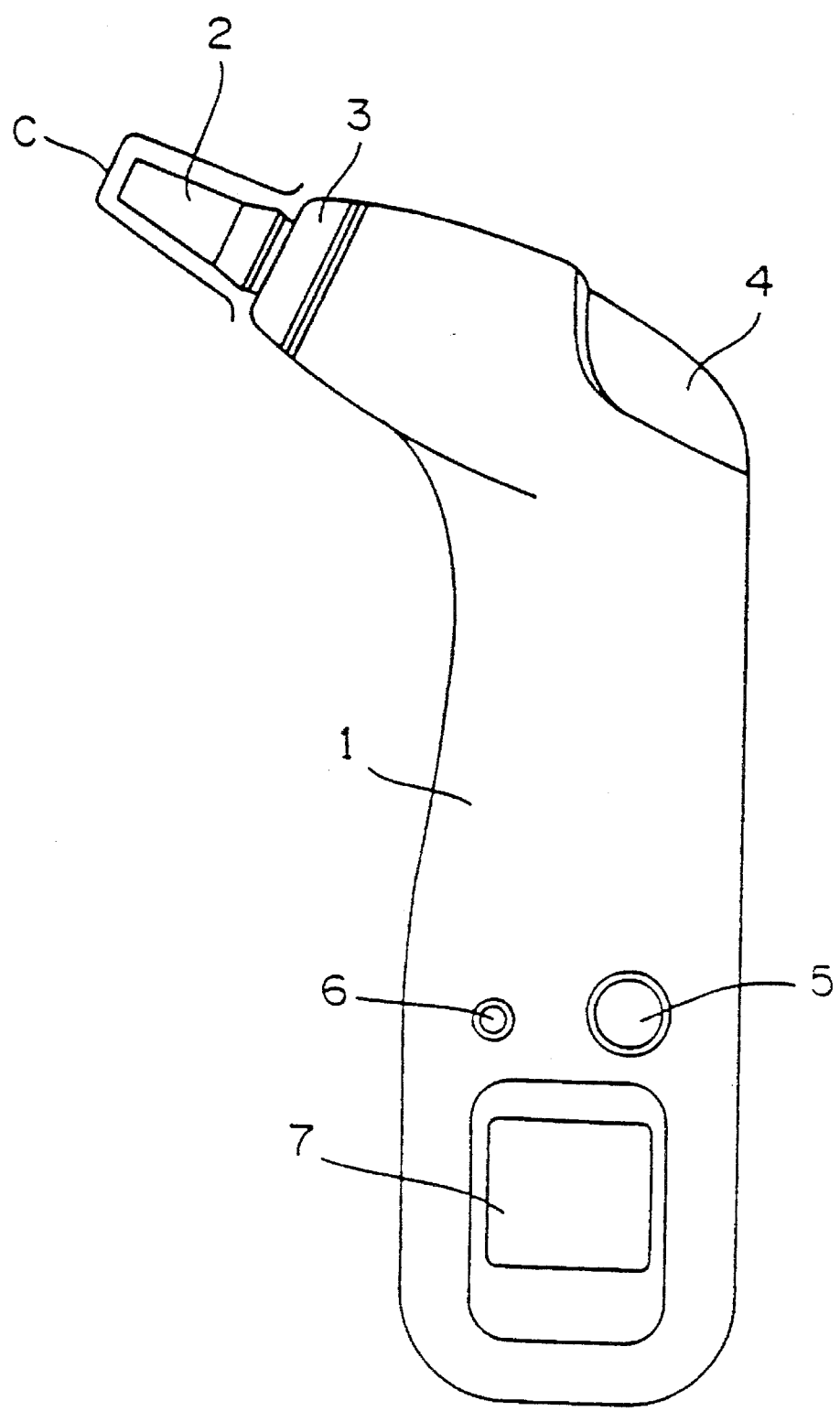
FIG. 1 is an external front view of a radiation clinical thermometer showing a first embodiment of the invention.
Figure 2:
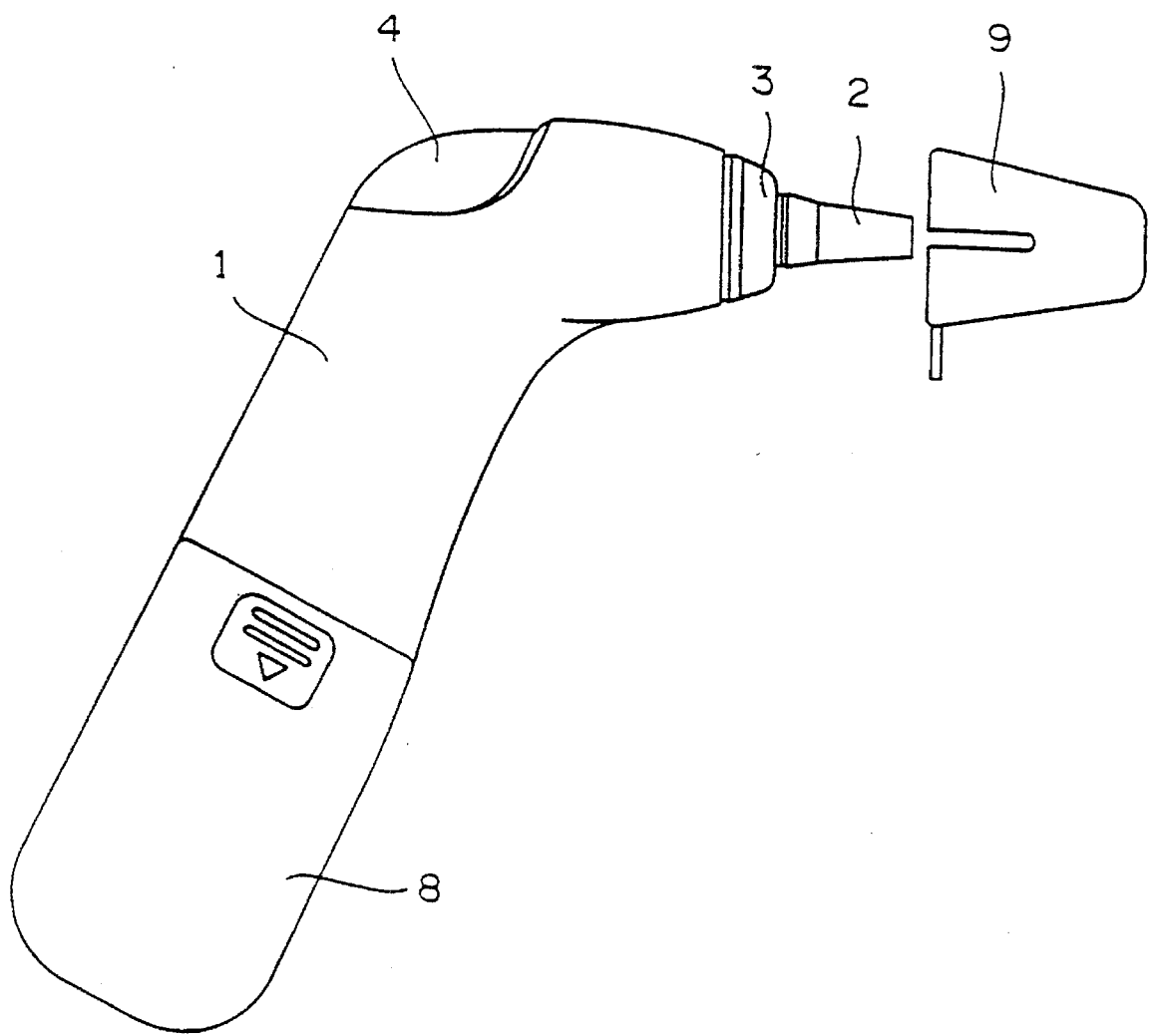
FIG. 2 is an external back view of the thermometer of FIG. 1.

Referring now to FIGS. 1 and 2, there are shown front and back external views of a radiation clinical thermometer as a first embodiment of the invention. The thermometer includes a body housing 1 enclosing a circuit and power source, a probe 2 enclosing an infrared sensor and externally projecting from the housing and adapted for movement in forward-and-backward directions, a release pipe 3 surrounding the probe 2 for movement in forward-and-backward directions, and a release button 4 for pushing out release pipe 3 toward the probe. A probe cover removable means includes the release pipe 3 and release button 4. On a front wall of the housing 1 of the thermometer there are provided a push button 5 for activating the power source, a push button 6 for illumination, and a LCD display 7. On a rear wall of the housing there is provided a batter cover 8 for replacement of a battery as the power source.

In the use of the thermometer as applied to a human body, probe 2 is biased slightly forwardly (outwardly) from housing 1 (via the force of a probe or start switch hereinafter described) and moves backwardly toward release pipe 3 when inserted into an ear opening. The small force produced on probe 2 by inserting the probe 2 into the ear is sufficient to move probe 2 backwardly against the start switch force and to thereby turn on the start switch. The start switch (probe operation state detection switch, described later) switches on and off in response to the forward-and-backward movement of the probe 2. Probe 2 is disposed within housing 1 so that the start switch is turned on when probe 2 moves backward (thereby generating a measurement start signal) and turned off when probe 2 moves forward (upon removing the probe from the ear). That is, once the force produced against the probe 2 due its insertion in the ear is removed, the force of the start switch, created by an internal biasing means in the start switch, moves the probe 2 outwardly while concurrently turning the start switch off.

Figure 3:
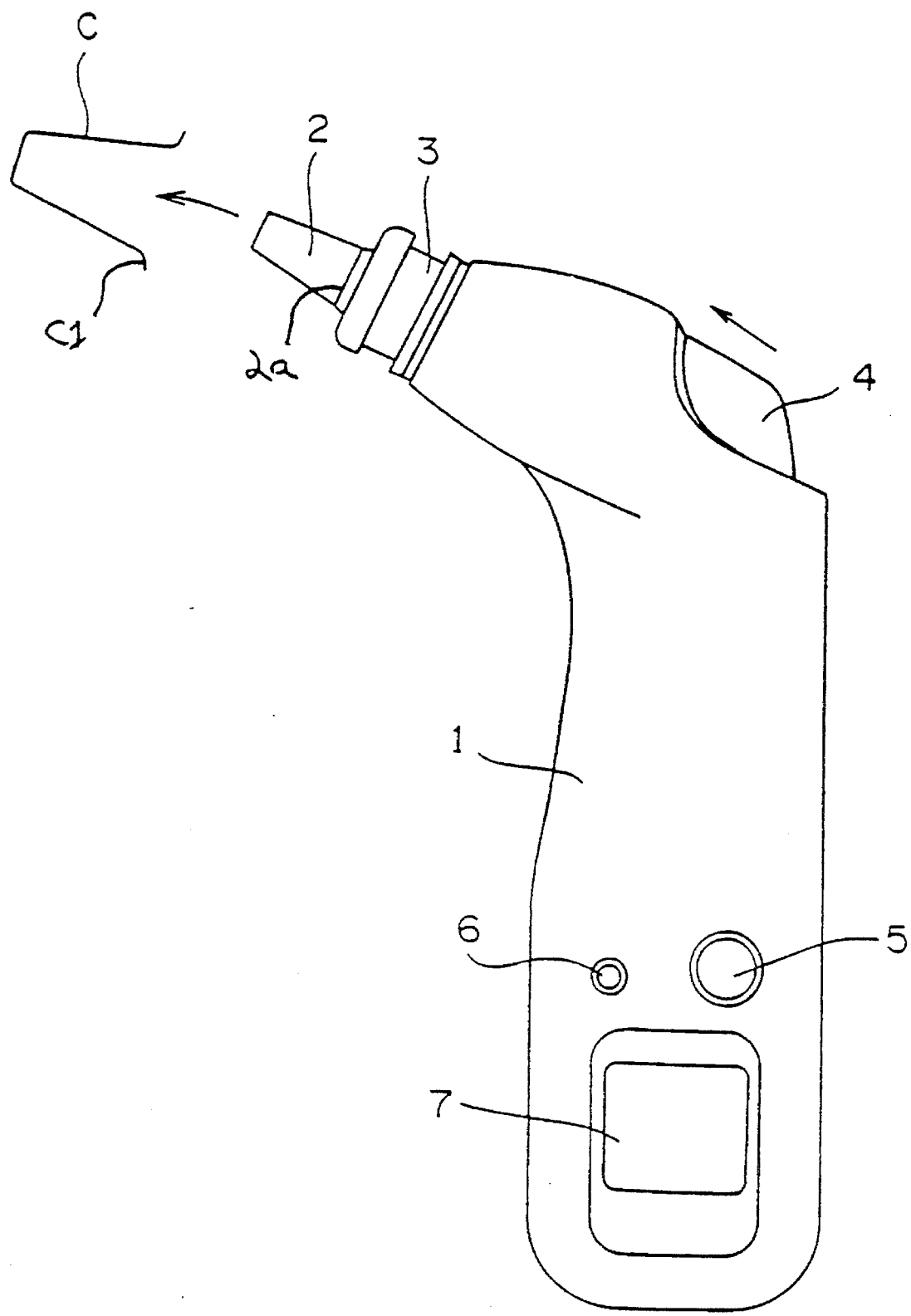
FIG. 3 is illustration showing a probe cover removed from the thermometer of FIG. 1.

As described above, the thermometer is designed so that when not in use (out-of-use mode) a cap 9 is mounted on probe 2 and when in use (measurement mode) a probe cover C is mounted on probe 2 for the prevention of stains to and sanitation of probe 2. The probe cover C is adapted to be dislodged from its mounted position on probe 2 by the action of release pipe 3 and release button 4. By pushing release button 4 in the direction of the arrow shown in FIG. 3, release pipe 3 is extended (moved forwardly) from body housing 1 and cover C is thereby ejected or released from probe 2. Upon pushing release button 4, release pipe 3 is locked in its projected state and can be returned to its original retracted position by releasing release button 4 and pushing release pipe 3 backwardly, toward body housing 1. Since release pipe 3, in actual use, is forced to move backwardly when the probe cover C is mounted, a separate step of pushing the release pipe 3 backwardly is not required. That is, the supply container which has a plurality of probe covers C contained therein is designed to receive probe 2 in order to mount a cover C thereon. The probe 2 is pressed into the container so that an annular portion C1 of cover C is forced into a retaining indentation 2a of probe 2 thereby mounting cover C in place. However, during this procedure the release pipe engages an outer surface of the container such that as the probe 2 is pushed into the container, release pipe 3 is moved backwardly.

Thus, when release pipe 3 is in the projected state it indicates that probe cover C is not mounted on probe 2, and when release pipe 3 is in retracted state it indicates probe cover C is mounted on probe 2. Accordingly, a cover switch within cover 1 (probe cover mount detection switch, described later) which is switched on and off in response to the forward-and-backward movement of release pipe 3 produces a signal representing whether or not cover C is mounted on probe 2.

The mechanism of probe 2, release pipe 3, release button 4 and so forth will be described hereinafter in more detail.

Figure 4:
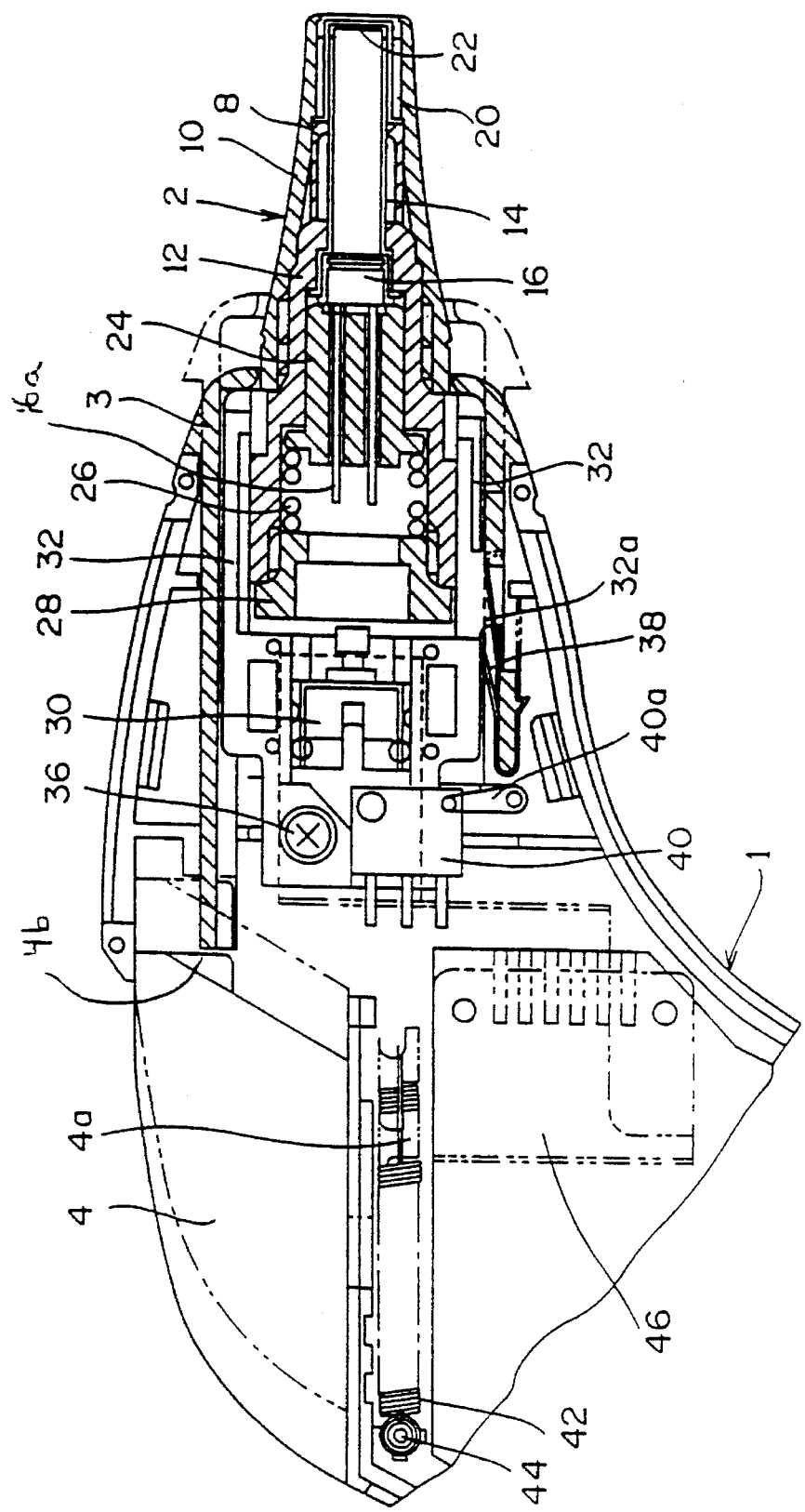
FIG. 4 is a partial longitudinal sectional view of the thermometer of FIG. 1.
Figure 5:
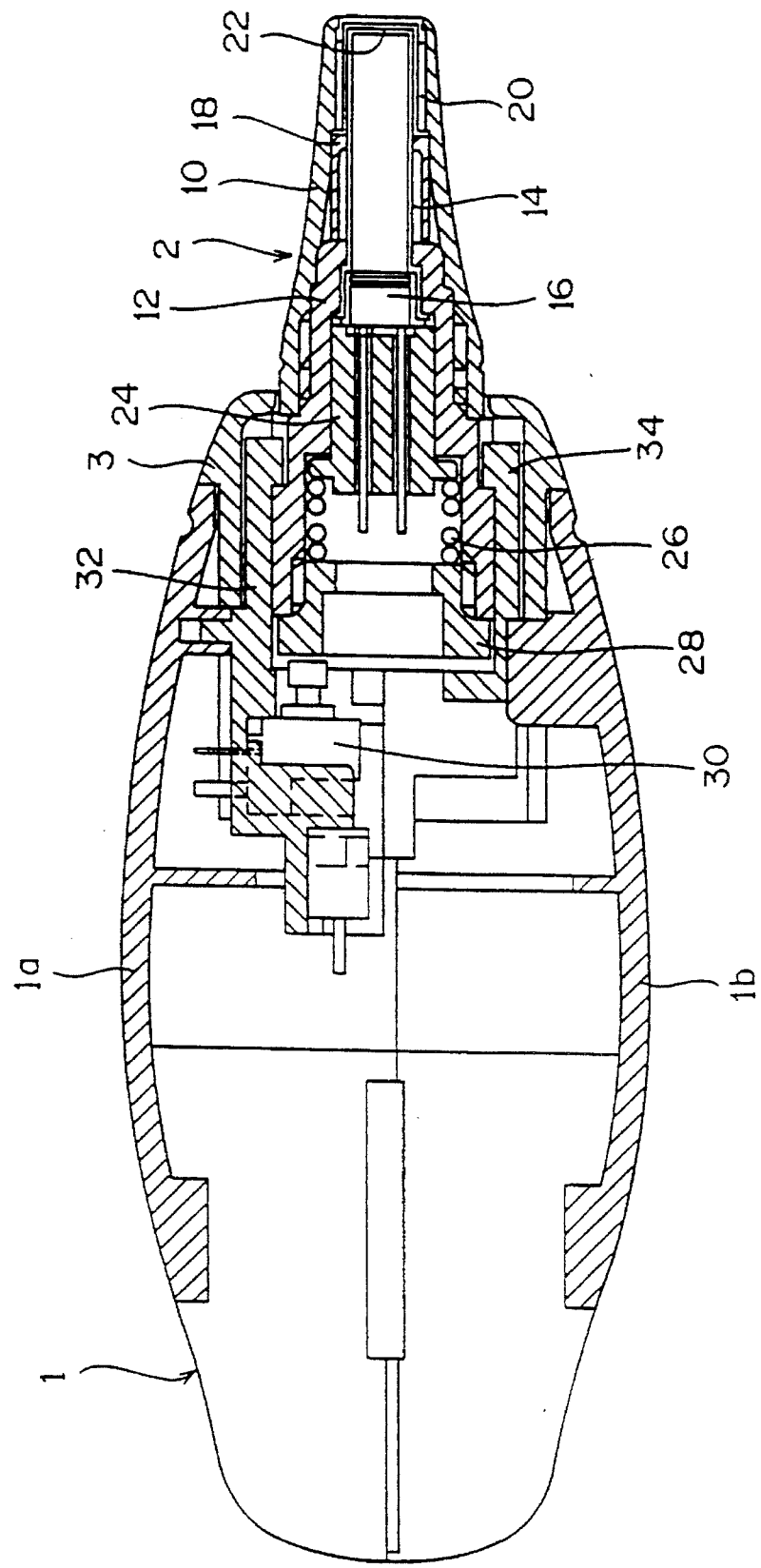
FIG. 5 is a partial cross sectional view of the thermometer of FIG. 1 as viewed from the top.

In FIGS. 4 and 5, body housing 1 consists of a front housing 1a and a ground housing 1b which are separably coupled to each other.

Probe 2 consists of a wrapping member 10 and a probe body 12 removably mounted by wrapping member 10. A wave guide 14 for guiding infrared radiation extends from probe body 12, and an infrared radiation sensor (temperature detection sensor) 16 is disposed at a rear end of guide 14. A wave guide cap 20 is mounted on guide 14 through a ring 18, and at its tip is mounted by a protection filter 22. Infrared radiation passes through protection filter 22 and is guided by wave guide 14 to reach infrared radiation sensor 16.

A lead frame 16a of infrared radiation sensor 16 is pierced thorough sleeve 24. Sleeve 24 is biased toward wave guide 14 by a spring coil 26 which is engaged with a rear end of the sleeve 24, such that infrared radiation sensor 16, which is disposed at a front end of sleeve 24, is pushed to a rear end of guide 14 and held thereby so that the whole probe 2 is biassed outside housing 1. Spring coil 26 is also engaged with a sensor cap 28 so as to be supported between sleeve 24 and sensor cap 28. Sensor cap 28 is engaged with a rear end of probe body 12. Probe or start switch 30 is disposed behind sensor cap 28 and is actuated by contact with sensor cap 28 as discussed below.

For a closing operation of start switch 30, probe 2 is subjected to a force which moves it backwardly toward housing 1, and consequently, sensor cap 28 is forced against start switch 30. When the force applied to probe 2 is sufficient to overcome the outward biassing force of start switch 30, start switch 30 will move backwardly 10 into a closed or on position. For an opening operation of start switch 30, the force which moves probe 2 backwardly is released so that probe 2 is returned to its original position by the biasing force of start switch 30 acting on sensor cap 28, such that start switch 30 moves to an open or off position.

Start switch 30 is fixed by a screw 36 to a probe base 32 mounted on front housing 1a. Probe base 32 is engaged with base cover 34 to produce a chamber therebetween in which a base end of probe 2 (end opposite to the end of probe 2 extending out of housing 1), is inserted.

Release pipe 3 is slidable in a forward-and-backward movement along probe base 32 and base cover 34 and has a blade spring 38 thereon which bends toward probe base 32. Cover switch (probe cover mount detection switch) 40 has a lever 40a that moves in response to the forward-and-backward movement of release pipe 3 and is mounted on probe base 32. In the retracted state of the release pipe 3 (probe cover is mounted), blade spring 38 is positioned behind a projection 32a formed on the base 32 and is locked in place. During the movement of release pipe 3 into the retracted state, lever 40a of a cover switch 40 is moved by a rear end of pipe 3 into the position shown in FIG. 4. In this state (switch 40 is turned on), switch 40 generates a probe cover mount signal which is indicative that probe cover C is mounted on probe 2. In a state where pipe 3 projects outwardly, (cover unmount state), blade spring 38 is positioned in front of projection 32a such that the rear end of pipe 3 does not contact lever 40a thereby allowing lever 40a to be automatically returned to its normal biased position due to the internal biasing means of cover switch 40. When lever 40a is in its normal biased position (switch 40 is off) it generates a cover unmount signal.

Release button 4 for pushing release pipe 3 forward is mounted on body housing 1 to be slidable thereon. A pulling spring 42 is engaged between an engagement member a disposed on release button 4 and a pin 44 disposed on front housing 1a and biases release button 4 away from probe 2. As release button 4 is pushed against the force exerted by spring 42, a tip 4b of release button 4 comes into contact with a rear end of release pipe 3 to push release pipe 3 forward so that it can be locked in its projected state as previously described. Upon the release of release button 4, it returns to its original position due to the action of spring 42.

A flexible base 46 is wired to electrically connect infrared radiation sensor 16, start switch 30 and cover switch 40 on a circuit board (not shown in the drawings). Electronic components are mounted on the circuit board in a predetermined pattern for providing a temperature measurement and the board is fixed in the front housing 1a of the housing 1.

The above-mentioned radiation clinical thermometer operates such that a temperature measurement is not initiated, even if a body temperature measurement start signal is generated by start switch 30, when a cover unmount signal is produced by cover switch 40 to indicate that the probe cover C has not been mounted on probe 2. This control is executed by circuits, and its operation will be explained hereinafter according to the flow chart of FIG. 6.

Upon the initial depression of the power button 5 in order to turn on power to the thermometer, predetermined information is displayed on LCD display 7. As shown in step ST1 the initial information can be some type of temperature display as well as an indication that the unit and battery are in a ready state.

In step ST2 various values are initialized. In step ST3 the circuits check to see if the probe cover detection switch 40 is in the closed or on position to indicate that the probe cover C is mounted an probe 2. If the probe cover detection switch 40 is on, a cover mount signal is generated. If, however, the probe cover switch 40 is open (off), a cover unmount signal is generated by the circuits. As previously discussed, the probe cover detection switch 40 is closed when the released pipe 3 is in its retracted position, and is open when release pipe 3 is in its projection position.

If a cover unmount signal (NO branch of flowchart) is determined to be present in step ST3, the sequence goes to step ST12 where the display will show that probe cover C is not mounted on probe cover 2 by, for example, displaying the word "CAP". Then, in step ST13 the display will, for example, show the last measured temperature, or in the situation where the battery has just been replaced might display --.--° F. or --.--° F. Since a "READY" display is not indicated in step ST13, it shows that the thermometer is not ready to take a temperature measurement.

After step ST13, if the power supply is turned off, the display, as shown in step ST15, will be blank. On the other hand, if the power remains on after step ST13, the circuits return to step ST3. Quite naturally, if the probe cover detection switch 40 is never turned on, the above described loop (ST3, ST12, ST13, ST14) will continually be repeated until the power is turned off or the probe cover detection switch 40 is turned on.

Assuming that the probe cover detection switch 40 is turned on, a cover mount signal (YES branch of flowchart) is determined to be present at step ST3. Then, in step ST4 a determination is made as to whether the probe start switch 30 is in the on or off position. If probe start switch 30 is not initially in an off position (probe start switch 30 open) it means that the probe 2 is being pressed on such that sensor cap 28 has pushed probe start switch 30 to the closed position. Since the inquiry of step ST4 occurs immediately after detection of the probe cover detection switch 40 being turned on, an indication of the closed position of probe start switch 30 may indicate that the probe start switch 30 was inadvertently pressed on during the mounting of the probe cover c. If such is the case, temperature measurement is not desired since probe 2 is not placed within the ear. Therefore, if in step ST4 the NO branch of the flowchart is followed, the sequence proceeds directly to step ST13 where an indication of the thermometer's readiness for temperature measurement is not indicated. In order for the thermometer to distinguish between an inadvertent closing of probe start switch 30 and a desired closing (step STS), a counting means is incorporated in the circuitry to determine if the probe start switch 30 was in an open position for a predetermined period of time. This feature is discussed in more detail below and in relation to FIG. 7.

If the YES branch of ST4 is followed indicating that the probe start switch is off, the circuits proceed to step ST6 where the last temperature measured is displayed along with the words "READY". The "READY" indication lets the user know that the thermometer is now ready to measure temperature. It should also be noted that after replacement of the battery, the display in step ST6 will be "--.-° F." or "--.-° C." along with the "READY" indication.

After step ST6, if during step ST7, it is determined that the power is turned off, the sequence proceeds to step ST15. However, as long as the power is on, the sequence checks in step ST8 to see if the probe start switch 30 is in the on or off position. If the probe start switch is off, the unit returns to step ST3. As long as the probe cover detection switch 40 is on and the probe start switch 30 is off, the unit will remain in the loop of ST3, ST4, ST6, ST7 and ST8 where the display of ST6 remains on. However, if the probe start detection switch 30 is moved to the on position, such as for example, by the probe 2 being placed in an ear, the sequence will proceed to step ST9, such that during the temperature measuring process of step 10 the display will show in step ST9, for example, "---° F." or "---° C.".

After temperature measurement (body temperature) has been completed, an audible beep (ST10A) is generated to indicate the end of temperature measurement. Then, in step ST11 the measured temperature is displayed in either ° C. or ° F.

After step ST11, the unit returns to step ST3 regardless of whether the probe start switch 30 is in the on or off position. If however, the probe start switch 30 was never returned to the off position, the sequence will proceed from step ST4 directly to ST13. However, if the probe start switch 30 at least once returned to the off position after step ST11, the unit will be in the loop ST3, ST4, ST6, ST7 and ST8 such that once the start switch 30 is subsequently depressed to the on position, a temperature measurement will be taken (assuming the probe cover detection switch is on).

Figure 6:
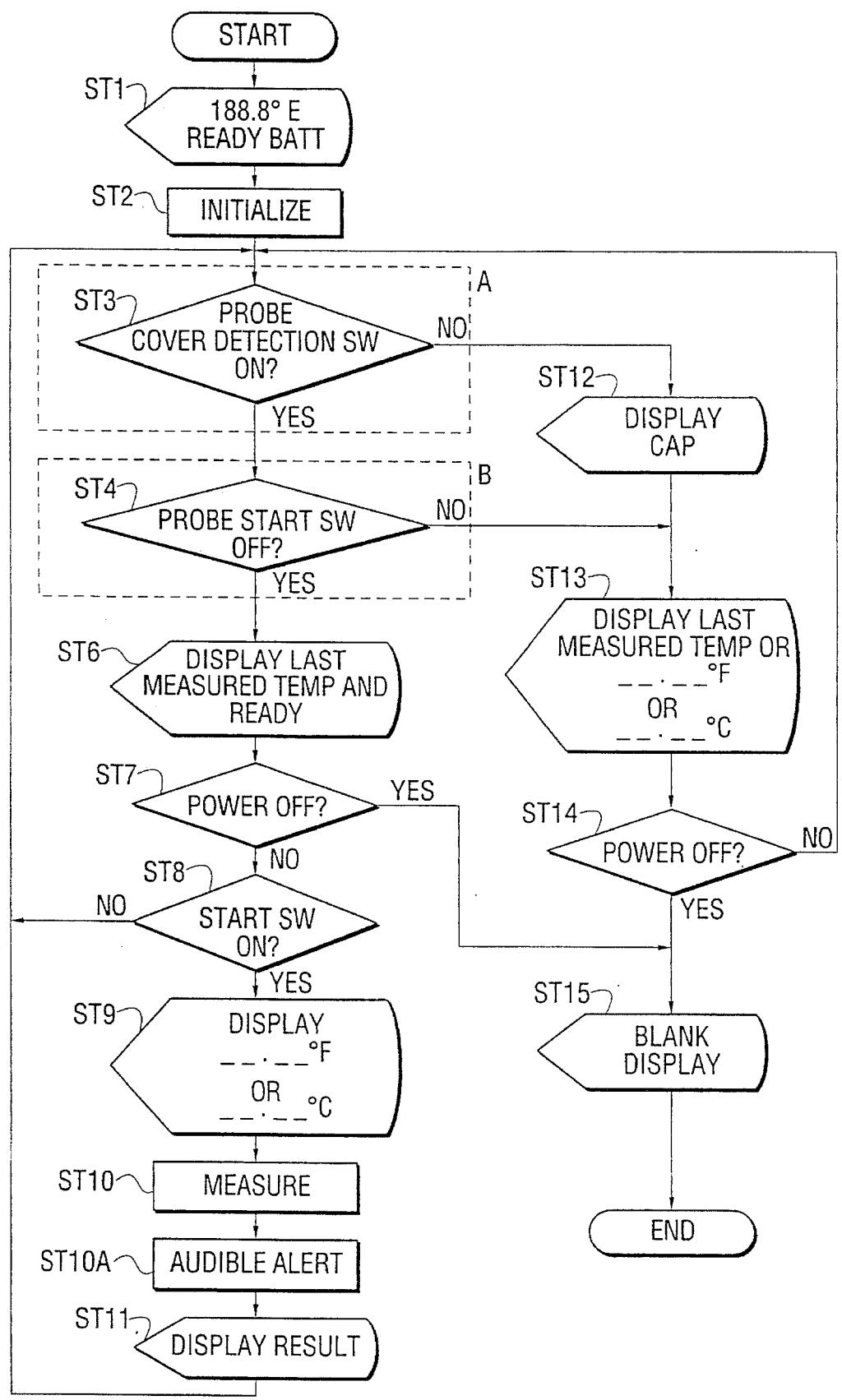
FIG. 6 is a flow chart of a body temperature measurement operation of the thermometer of FIG. 1.

Thus, the flowchart of FIG. 6 shows that temperature measurement is not initiated even when start switch 30 is turned on as long as probe cover C is not mounted on probe 2 (switch 40 not on), thereby preventing temperature measurement in a cover unmount state.

Figure 7:
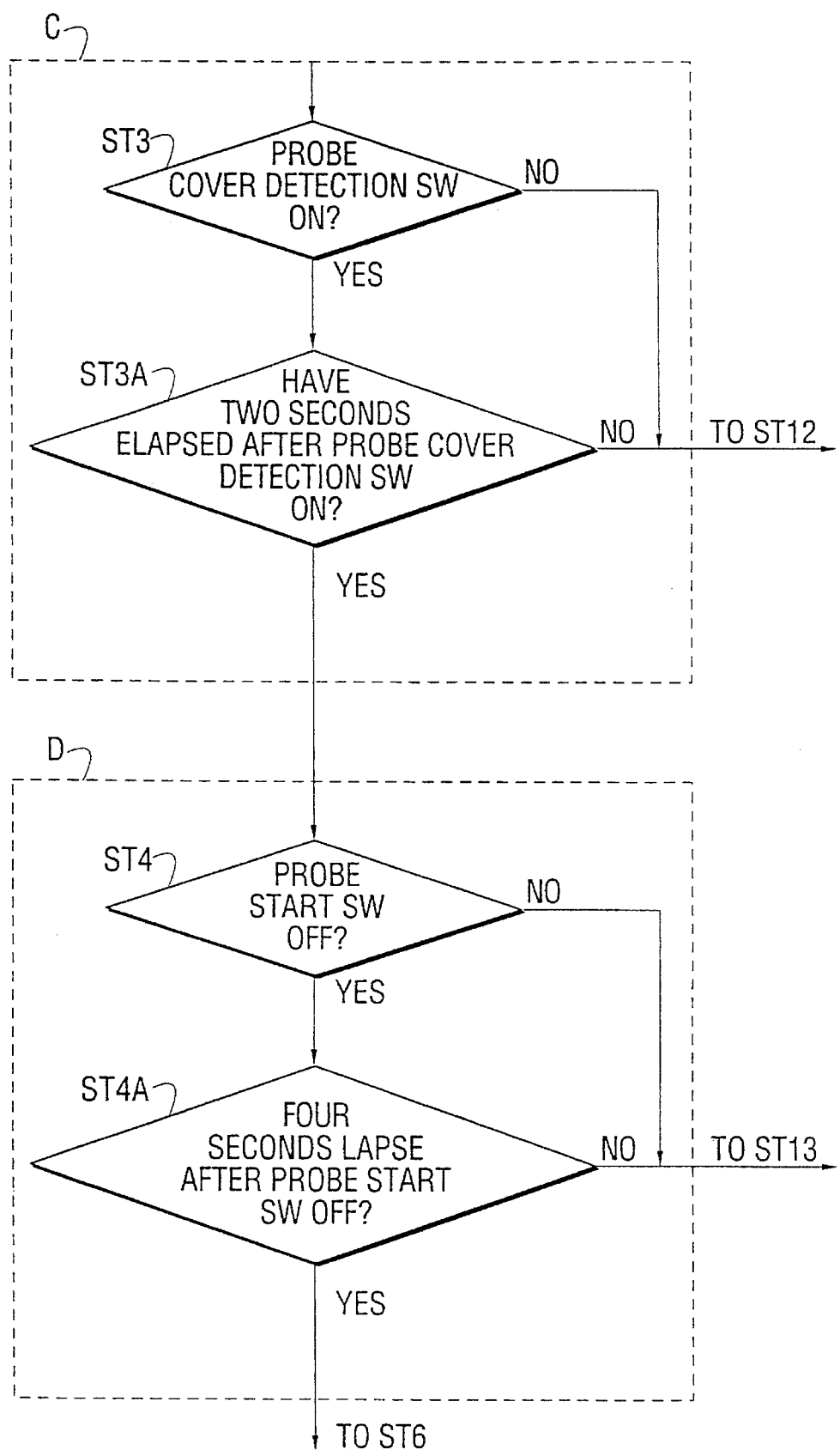
FIG. 7 is a flow chart of alternative steps C and D which can be substituted in place of steps A and B, respectively, of the flow chart of FIG. 6, to represent a second embodiment of the invention.

FIG. 7 shows step blocks C and D which respectively can replace step blocks A and B of FIG. 6 to produce a second embodiment of the invention which incorporates a time delay feature. That is, in step C, step ST3 is performed to determine if a probe cover C is mounted on probe 2. However, unlike FIG. 6, if the answer to the inquiry in ST3 is yes, a second step ST3A follows. In step ST3A, it is determined if the probe cover detection switch 40 has been switched on for a predetermined period of time (i.e. two seconds). If the predetermined period of time has elapsed, the sequence moves to step ST4 of step block D. If however, the NO branch of steps ST3 and ST3A are followed, the sequence moves to step ST12.

Step ST4 of step block D is the same as step ST4 of step block A of FIG. 6. However, if step ST4 of step block D answers the inquiry along the YES branch of the flowchart, the sequence moves to step 4A where a determination is made as to whether, for example, four seconds have passed since the probe start switch 30 has been turned off. If a NO determination is made as a result of either of the inquiries of Steps 4, 4A, the sequence goes to ST13. However, if a YES determination is made in Step ST4A, the sequence moves to ST6 where an indication that the thermometer is ready to measure temperature is displayed.

The temperature measurement delay step ST3A ensures that if the thermometer is roughly handled, an instantaneous and inadvertent closure of the probe cover detection switch 40 is not automatically taken as an indication that the probe cover C has been mounted. Rather, the probe cover C is only considered mounted if the probe cover detection switch is turned on for a predetermined period of time.

The temperature measurement delay of step ST4A serves a similar purpose to that on step ST3A. In step ST4A however, a determination is made as to whether the probe start switch 30 is in the off position for a predetermined period of time. In the situation where the probe cover C is being mounted, it is possible that the probe 2 can be inadvertently contacted such that the probe start switch 30 is instantaneously turned on and off, possibly even in a repetitive manner. Step ST4A therefore ensures that at least, for example, four seconds must elapse after the probe start switch 30 is turned off prior to moving to the ready step ST6. Therefore, if intermittent short movements of the probe 2 occur while placing the probe cover C on probe 2 such that the probe start switch 30 is intermittently turned on and off at less than 4 second intervals, the thermometer will not begin measuring temperature.

It is be noted that conventional counting means can be incorporated in the temperature measuring circuitry to determine if the predetermined elapsed times of steps 3A and 4A have been met.

According to the radiation clinical thermometer, unnecessary measurement which is generally apt to happen during mounting of the probe cover on the probe is prevented. Though erroneous measurement is conventionally executed when measurement is executed when the probe is uncovered, such erroneous measurement can be avoided in the inventive thermometer because measurement is prohibited when the probe cover is not mounted. Moreover, the radiation clinical thermometer prevents unnecessary temperature measurement due to the instantaneous and intermittent closing and opening of both the probe cover start switch and the probe detection switch which can occur during the mounting of the probe cover or due to rough handling of the thermometer.

Additional advantages and modifications will readily occur to those skilled in the art. Therefore, the invention in its broader aspects is not limited to the specific details, and representative devices, shown and described herein. Accordingly, various modifications may be made without departing from the spirit or scope of the general inventive concept as defined by the appended claims and their equivalents.

What is claimed is:

1. A radiation clinical thermometer comprising:

a body housing;

a temperature measuring circuit secured in said body housing;

a probe secured to said body housing;

a temperature sensor disposed in said probe;

a power supply secured in said body housing and connected in circuit with said temperature measuring circuit and said temperature sensor;

means for detecting if a probe cover is mounted on said probe;

means, operatively connected to said detecting means, for determining a condition to enable operation of said thermometer; and means, operatively connected to said determining means, for enabling operation of said thermometer.

2. A radiation clinical thermometer as recited in claim 1, wherein said detecting means includes a probe cover removable means for dismounting a probe cover from said probe, said probe cover removable means including a member moveable from a first position in which said probe cover is not mounted on said probe to a second position in which said probe cover is mounted on said probe, and a probe cover mount detection switch being engageable with said probe cover removable means when said probe cover removable means is moved into said second position thereby actuating said probe cover mount detection switch; and wherein said determining means is operatively connected to said probe cover mount detection switch to enable operation of said thermometer only upon said condition being that said probe cover removable means is in said second position.

3. A radiation clinical thermometer as recited in claim 2, wherein said first position is an extended position away from said body housing, said second position is a retracted position toward said body housing, and said member is moveable along a longitudinal direction of said probe between said retracted and extended positions.

4. A radiation clinical thermometer as recited in claim 3, wherein said probe cover removable means further comprises a release button biased away from said member but moveable into contact with said member to move said member from said retracted position to said extended position.

5. A radiation clinical thermometer as recited in claim 1,
wherein said enabling means includes a start switch connected in circuit with said power supply, said temperature sensor and said temperature measuring circuit; wherein said probe is operatively coupled to said temperature sensor and movably secured in said body housing, said probe being biased for movement outwardly of said body housing in a projected state prior to temperature measurement in which said start switch is not actuated and moveable to a retracted state by insertion of said probe into an ear opening of a patient, said retracted state actuating said start switch to enable operation of said thermometer; and wherein said determining means engages said enabling means to enable operation of said thermometer upon the condition that said start switch is actuated after said start switch was not actuated for a predetermined period of time and only when said detecting means has detected that said probe cover is mounted on said probe.

6. A radiation clinical thermometer as recited in claim 1, wherein said detecting means includes a probe cover removable means for dismounting a probe cover from said probe, said probe cover removable means including a member moveable from a first position in which said probe cover is not mounted on said probe to a second position in which said probe cover is mounted on said probe, and a probe cover mount detection switch being engageable with said probe cover removable means when said probe cover removable means is moved into said second position; and wherein said determining means determines as said condition whether said probe cover mount detection switch has been actuated for a predetermined period of time and engages said enabling means to enable operation of said thermometer only when said probe cover mount detection switch has been actuated for said predetermined period of time and said probe cover removable means is in said second position.

7. A radiation clinical thermometer as recited in claim 6, wherein said first position is an extended position away from said body housing, said second position is a retracted position toward said body housing, and said member is moveable along a longitudinal direction of said probe between said retracted and extended positions.

8. A radiation clinical thermometer as recited in claim 7, wherein said probe cover removable means further comprises a release button biased away from said member but moveable into contact with said member to move said member from said retracted position to said extended position.

9. A radiation clinical thermometer as recited in claim 1,
wherein said determining means determines as said condition whether a probe cover has been mounted on said probe for a predetermined period of time and engages said enabling means to enable operation of said thermometer only when said probe cover has been mounted on said probe for said predetermined period of time.

10. In a radiation clinical thermometer having a body housing, said body housing securing a display, a temperature measuring circuit, a temperature sensor, and a start switch connected in circuit with a power source, said body housing further securing a probe biased for movement outwardly of said body housing in a projected state prior to temperature measurement in which said start switch is not actuated and moveable to a retracted state by insertion of said probe into an ear opening of a patient, said retracted state actuating said start switch, the radiation clinical thermometer further comprising:

probe cover removable means for dismounting a probe cover from said probe, said means including a member moveable from a first position in which said probe cover is dismounted to a secured second position in which said probe cover is secured on said probe; and a probe cover mount detection switch engageable with said probe cover removable means when said probe cover removable means is in said second position and electrically connected in circuit with said start switch for enabling operation of said thermometer only when said probe is in said retracted state and said probe cover removable means is in said second position.

11. A radiation clinical thermometer as recited in claim 10, wherein said first position is an extended position away from said body housing, said second position is a retracted position toward said body housing, and said member is moveable along a longitudinal direction of said probe between said retracted and extended positions.

12. A radiation clinical thermometer as recited in claim 11, wherein said probe cover removable means further comprises a release button biased away from said member but moveable into contact with said member to move said member from said retracted position to said extended position.

13. In a radiation clinical thermometer having a body housing, said body housing securing a display, a temperature measuring circuit, a temperature sensor, and a start switch connected in circuit with a power source, said body housing further securing a probe biased for movement outwardly of said body housing in a projected state prior to temperature measurement in which said start switch is not actuated and moveable to a retracted state by insertion of said probe into an ear opening of a patient, said retracted state actuating said start switch, the radiation clinical thermometer further comprising:

probe cover removable means for dismounting a probe cover from said probe, said means including a member moveable from a first position in which said probe cover is dismounted to a secured second position in which said probe cover is secured on said probe;

a probe cover mount detection switch engageable with said probe cover removable means when said probe cover removable means is in said second position and electrically connected in circuit with said start switch for enabling operation of said thermometer only when said probe is in said retracted state and said probe cover removable means is in said second position; and means for determining if said probe cover mount detection switch has been actuated for a predetermined period of time and for enabling operation of said thermometer only when said probe cover mount detection switch has been actuated for said predetermined period of time.

* * * * *